United States Patent [19]

Kollonitsch

[11] 4,096,180
[45] Jun. 20, 1978

[54] FLUORODEHYDROXYLATION OF SERINE

[75] Inventor: Janos Kollonitsch, Westfield, N.J.

[73] Assignee: Merck & Co., Inc., Rahway, N.J.

[21] Appl. No.: 756,446

[22] Filed: Jan. 3, 1977

Related U.S. Application Data

[63] Continuation of Ser. No. 586,326, Jun. 12, 1975, abandoned.

[51] Int. Cl.² .................. C07C 101/10; C07B 9/00
[52] U.S. Cl. .................. 260/534 C; 260/288 CE;
 260/293.51; 260/296 R; 260/302 R; 260/570.8
 R; 260/583 G; 260/651 F; 260/653; 544/327;
 548/342
[58] Field of Search .................. 260/534 C

[56] References Cited
U.S. PATENT DOCUMENTS 2,567,011   9/1951   Dresslin et al. .................. 260/465.7

OTHER PUBLICATIONS

Hasek et al., J. Am. Chem. Soc., 92, pp. 543-551 (1960).
Stacey et al., "Advances in Fluorine Chemistry," 1, pp. 158-160 (1960).
Raasch, J. Org. Chem., 27, pp. 1406-1409 (1962).
Boswell, "Organic Reactions," vol. 21, pp. 1-124 (1974, John Wiley & Sons).

Primary Examiner—James O. Thomas, Jr.
Assistant Examiner—Michael Shippen
Attorney, Agent, or Firm—Hesna J. Pfeiffer; Julian S. Levitt

[57] ABSTRACT

Organic compounds containing one or more alcoholic hydroxyl groups are transformed into fluorine compounds by reacting them with sulfur tetrafluoride in liquid hydrogen fluoride solution, at temperatures between around −80° C. and +20° C. The method can be descriptively termed "fluorodehydroxylation", because it represents the reaction:

ROH→RF.

7 Claims, No Drawings

FLUORODEHYDROXYLATION OF SERINE

RELATIONSHIP TO PRIOR APPLICATIONS

This application is a continuation of U.S. Ser. No. 586,326, filed 12, 1975, abandoned January 16, 1977.

DESCRIPTION OF THE PRIOR ART

A recently published review monograph, Organic Reactions, Vol. 21, John Wiley & Sons, 1974, contains the article, Bowswell et al., "Fluorination by Sulfur Tetrafluoride", pp 1–124. The applicability of the reagent for fluorination of alcohols is discussed, pp 12–13. It is pointed out there that only highly acidic alcohols (having a $PK_a = 6.42$ or higher) are useful substrates for transformation of an alcohol to the corresponding fluorine derivative. By contrast, $SF_4$ has been used extensively over the last decade or more to effect the transformations of aldehydes, ketones and carboxylic acids to the corresponding fluorine compounds, e.g.:

$$R-COOH \longrightarrow R-CF_3$$

$$R-\underset{\underset{O}{\|}}{C}-R \longrightarrow R-CF_2-R$$

$$R-C\overset{H}{=}O \longrightarrow R-CHF_2$$

(See above cited review article, pp. 20–36). In the fluorinations discussed in the literature, $SF_4$ has been employed, in some instancces, with a catalyst such as HF, $HF_3$, $ASF_3$, $PF_5$ and $TiF_4$. One example of the catalyzed reaction is found in U.S. Pat. No. 3,211,723, in which steroids containing a ketone group were fluorinated using $SF_4$ and approximately equivalent amounts of HF.

In the literature, as discussed above and elsewhere, the reactions are described as taking place at relatively high temperature, i.e., ambient up to 350° C. The reagent $SF_4$ is usually introduced into the reaction vessel at a low temperature ($SF_4$ is a gas at room temperature), but the reaction is run at higher temperature. The temperature range most frequently employed is 100°–200° C.; thus, considering the low boiling point of $SF_4 (-38°$ C.) a closed reaction vessel is employed. Five to ten hours reaction time is average.

SUMMARY OF THE INVENTION

It has been found now that organic compounds containing oen or more alcoholic hydroxyl groups are transformed into organic fluorine compounds: $R-OH \rightarrow RF$ by reacting their solution in liquid HF with $SF_4$. One surprising fact of this novel procedure is the fast rate of reaction ("fluorodehydroxylation"), even when employing very low temperatures, e.g., the range between $-80°$ C. and $+20°$ C. This high rate of reaction at low temperature, in turn, allows the reaction to run at ambient or lower temperatures, that is, in a temperature region where $SF_4$ is soluble, with the resulting economic advantage ensuing from the avoidance of costly high pressure autoclaves.

Another important feature of "fluorodehydroxylation" is its unusual selectivity. In the prior art, the usual reaction of $SF_4$ with carbonyl and carboxyl compounds leads to fluorination, e.g., J.A.C.S. 82, 543 (1960),

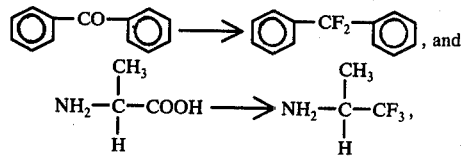

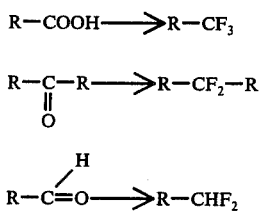

Journal of Organic Chemistry, 27, pp. 1406–1409, (1962). Upon practice of the process of this application, "fluorodehydroxylation", these groups remain intact, as demonstrated on benzaldehyde and w-aminoacetophenone. This reversal of the usual order of reactivity is illustrated by the reaction (later described in detail) of serine in $HF-SF_4$ at $-80°$ C., to yield 3-fluoro-D-alanine. The carboxyl group, which in "normal" $SF_4$ chemistry would be transferred into a $-CF_3$ group, remained intact, whereas the normally non-reactive alcoholic hydroxyl group is transformed in a fluoro group. Thus, under the conditions of this invention,, the reactivity and utility of $SF_4$ is the opposite of the normally observed behavior. Compare, for instance, the statement Raasch, "The Chemistry of Sulfur Tetrafluoride IX, Reaction with Amino Acids in Hydrogen Fluoride", Journal of Organic Chemistry, 27, pp. 1406–1409 (1962) wherein it is shown that amino acids were in general fluorinated on their carboxyl groups even in $SF_4-HF$ systems.

The compounds which can be successfully fluorodehydroxylated in this reaction include organic alcohols having at least one —OH groups present, attached to an aliphatic, aromatic, heteroaliphtic, or heterocyclic group. Without limiting the scope of the invention, a list of suitable compounds includes L-ephedrine, D-ephedrine, t-butylaminoethanol, D-serine, 2-deutero-D-serine, quinine, D,L-serine, 2-deutero-D,L-serine, L-serine, and 2-deutero-L-serine hexan-1-ol, 2-amino-1-phenylethanol, pyridoxamine, pyridoxine, hexafluoro-2-phenylisopropanol, choline, thiamine, β-hydroxyhistamine, 4-hydroxy-piperidine, 4-methyl-5(2-hydroxyethyl)-thiazole, threo-phenylserine, 3-aminopropanol, aliphatic, cycloaliphatic, as well as other heterocyclic alcohols, amino alcohols, or amino acids containing one or more alcoholic hydroxyls, and other similar compounds.

The reaction takes place by taking the chosen reactant, dissolving or mixing it in a molecular excess of liquid HF, and then adding at least one equivalent, or up to 3 molecular equivalents, of liquid $SF_4$. Preferably, the temperature of the HF and the $SF_4$ are between $-30°$ C. and $-80°$ C. before each addition. The reaction mixture is kept at the desired temperature within the operable range until the reaction is complete, within ½ – 48 hours. Hastalloy, steel, KEL-F ®, TEFLON ® or any other material normally employed for reactions in liquid HF can be utilized as material of construction for reactors used.

The novel process of this invention provides a convenient route to a large variety of organic fluorine compounds. Such compounds are known to have wide ranging utility, as for example, solvents, intermediates in organic synthesis, insecticides, plant growth regulators, herbicides refrigerants, lubricants, pharmaceuticals, and so on.

In addition, the product 3-(4-amino-2-methylpyrimidyl-5-methyl)-4-methyl-5-(2-fluoroethyl)thiazolium chloride hydrochloride, as prepared in Example 14, is a highly active coccidiostat.

EXAMPLE 1

Fluorodehydroxylation of L-Ephedrine

L-Ephedrine (1.65 g., 10 mg. mole) is dissolved in 20 ml. of liquid hydrogen fluorine, then while cooling in a dry-ice-acetone bath, 2.1 g. of $SF_4$ (~21 mg. mole) is passed into the stirred solution. After aging it overnight, the cooling bath is removed and the solvent evaporated with a stream of nitrogen gas. The residue is dissolved in 10 ml. of conc. aq. HCl, evaporated to dryness in vacuo. This treatment is repeated four times, to transform the HF salts to HCl salt. The residue consists, according to pmr spectrum (in $D_2O$/DCl) of the hydrochloride salts of the following two compounds:
erythro-fluorodeoxy-L-ephedrine; and
threo-fluorodeoxy-L-ephedrine.
The combined yield of the above two compounds is close to 100% of theory.

Recrystallization of the mixture from isopropanol delivers one of the two diastereoisomers in pure state, m.p. 203°–205° (dec.). This novel compound was fully characterized by C—H—N—F—Cl analysis and pmr spectrum.

EXAMPLE 2

Fluorodehydroxylation of D-Ephedrine

D-Ephedrine, subjected to the same conditions as in Example 1, resulted a mixture of erythro-fluorodehydroxy-D-ephedrine and threo-fluorodeoxy-D-ephedrine, in the form of hydrochloride salt.

EXAMPLE 3

Fluorodehydroxylation of 2-(Tertiary Butylamino)ethanol 2-(T. butylamino)ethanol (1.20 g.; approximately 10 mg.-mole) is fluorodehydroxylated in 20 ml. of liquid HF, employing 1.2 ml. (at −78° C.) (21 mg. mole) of $SF_4$. The solution is left standing overnight, while cooled in a dry-ice-acetone bath.

After removal of the cooling bath, HF is removed by a stream of $N_2$ gas, the residue (HF salt) is transformed into HCl salt by dissolving in conc. HCl, evaporating this in vacuo. Repeating this operation three times, one obtains substantially pure hydrochloride of 1-fluoro-2-(t.butylamino) ethane. Crystallized from acetonitrile m.p. 214°–215° (dec.). This novel compound was fully characterized by pmr spectrum and C—H—N—F—Cl analysis.

EXAMPLE 4

Fluorodehydroxylation of D-Serine

D-serine (1.05 g.; 10 mg. mole) is dissolved in 20 ml. of liquid HF, cooled to approximately −78° C. (dry-ice-acetone cooling bath), then 1.2 ml. $SF_4$ (21 mg. mole) is passed in gaseous form. After standing overnight with dry-ice-acetone cooling, the solvent is removed by passing through a stream of nitrogen.

The residue represents substantially pure HF salt of 3-fluoro-D-alanine, in addition to some unchanged starting material. This salt mixture is transformed into the HCl salt by dissolving in 20 ml. of conc. aqueous HCl, evaporating in vacuo to dryness. This treatment is repeated three more times, then the dry residue is dissolved in water, pyridine and isopropanol (pH approximately 3.5) and the crystalline 3-fluoro-D-alanine isolated by filtration. For analysis, it is recrystallized from water-isopropanol. The product 3-fluoro-D-alanine was characterized by C—H—N—F analysis, pmr spectrum and optical rotation. ($[\alpha]_D^{23°}$: −10.2° in 1M aq. HCl).

EXAMPLE 5

Fluorodehydroxylation of 2-Deutero-D-Serine

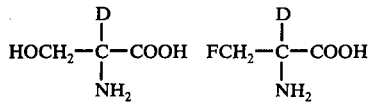

2-Deuterated analog of D-serine is fluorodehydroxylated in a manner described above, to give 3-fluoro-2-deutero-alanine. The product is characterized by C—H—N—F analysis and pmr spectrum. The D-serine-2-d starting material is obtained by subjecting D,L-serine-2-d [Walsh et al., Journal of Biological Chemistry, 246, p. 6857 (1972)] to the enzymatic resolution method employed originally for resolution of D,L-serine [Greenstein and Winitz, Chemistry of Amino Acids, Vol. 3, pp. 2230–2232, Wiley, New York, New York, (1961)].

EXAMPLE 6

Fluorodehydroxylation of 2-Hydroxymethyl-Imidazole

2-Hydroxymethylimidazole (0.98 g.; 10 mg. mole) is dissolved in 20 ml. of liquid HF, then $SF_4$ gas (26 mg. mole) is passed in and the solution left standing overnight. The whole operation is performed while cooling in dry-ice-acetone bath. Next morning another amount (18 mg. mole) of $SF_4$ was added and the solution left standing again overnight (dry-ice-acetone cooling bath). The solvent was removed by passing through $N_2$ gas and the residual HF salt transformed into HCl salt by adding 10 ml. of conc. aq. HCl, evaporating to dryness in vacuo. This treatment is repeated three more times, to leave a residue of substantially pure 2-fluoromethylimidazole HCl. For purification, it is treated with 15 ml. of hot isopropanol, the filtrate concentrated to dryness in vacuo and recrystallized from acetonitrile, to give 2-fluoromethylimidazole HCl, which is a new compound. It was characterized using C—H—N—F—Cl analysis and pmr spectrum.

EXAMPLE 7

Fluorodehydroxylation of Quinine

Quinine (6.5 g.; 20 mg. mole) is dissolved in 35 ml. of anhydrous HF while cooling in a dry-ice-acetone bath. Under continuing cooling and stirring $SF_4$ gas is passed in (85 mg. mole; 4.8 ml. liquid $SF_4$ at −78° C.) and the solution left standing overnight in the dry-ice-acetone cooling bath. After removal of cooling, the solvent is removed by stream of $N_2$ gas, the residue dissolved in aq. cc. HCl, evaporated to dryness in vacuo. The hydrochloride thus obtained is dissolved in a mixture of 20 ml. isopropanol with 5 ml. of water, the hazy solution is filtered with Celite, then with active carbon (DARCO G 60); naphthalene 1,5-disulfonic acid (8.85 g.) is added to the substrate, to yield crystalline naphthalene-disulfonate salt of fluorodeoxy-quinine, yield 11.4 g. This novel product was fully characterized by pmr spectrum and C—H—N—F—S analysis.

EXAMPLE 8

Fluorodehydroxylation of Hexan-1-ol

Pyridine (50 ml.) is charged into a Kel-F reactor, cooled by immersion into a dry-ice-acetone bath; 100 ml. of HF is added, followed by hexan-1-ol, (10.2 g. ~ 100 mg. mole). $SF_4$ gas is passed in (8 ml. at −78° C.; 142 mg. mole) and the mixture left aging overnight at −78° C. The solution is poured into a separatory funnel (TEFLON ®) and drained slowly into crushed ice. It is extracted with $CH_2Cl_2$ (2 × 100 ml.), backwashed with water, dried over $MgSO_4$. The solvent is removed by distillation, to result a mixture containing some unreacted starting material, 2-fluorohexane and 3-fluorohexane. Fractionated distillation (spinning-band column) delivers 2-fluorohexane and 3-fluorohexane. Characterization by C—H—F analysis and pmr and $F^{19}$ mr spectroscopy.

EXAMPLE 9

Fluorodehydroxylation of 2-Amino-1-Phenylethanol

A mixture of anhydrous HF (20 ml.) and 1.4 ml. (25 mg.-mole) of $SF_4$ is prepared in a KEL-F reactor at −78° C. Dry-ice-acetone bath is employed. While continuing cooling, 2-amino-1-phenylethanol (1.37 g., 10 mg.-mole) is added with stirring. After aging the reaction mixture for 45 minutes at −78° C., the solvent is removed by a stream of $N_2$ gas. Conc. aqueous HCl is added to the residual syrup and concentrated to dryness, to give a product consisting of a mixture of the HCl and HF salts of 2-amino-1-phenyl-1-fluoroethane, characterized by C—H—N—F—Cl analysis and pmr spectrum.

EXAMPLE 10

Fluorodehydroxylation of Pyridoxamine

Pyridoxamine-2 HCl (5.112 g.; 21.2 mg.-mole) is dissolved in liquid HF (60 ml.); $SF_4$ (2.6 ml. at −78° C.; 46 mg.-mole) is passed in (dry-ice-acetone bath). After overnight aging at −78° C., the solvent is removed by a stream of nitrogen gas, the residue is dissolved in 100 ml. of aq. cc. HCl and evaporated to dryness to vacuo. To complete the transformation of the HF salt into the hydrochloride, the residue is dissolved in water and passed through a Dowex 50 × 2 resin column ($H^{\oplus}$ form); the column is washed free of HF. The product is released then by elution with 4M aq. HCl. The UV absorbing eluate fractions are combined and evaporated to dryness in vacuo and the product recrystallized from a methanol-ethanol mixture. The crystalline product: 2-methyl-3-hydroxy-4-amino-methyl-5-fluoromethyl-pyridine-dihydrochloride, (novel compound), does not melt up to 260° C.; it was characterized by C—H—N—F—Cl analysis and pmr spectrum.

EXAMPLE 11

Preparation of 2-Methyl-3-Hydroxy-4-Hydroxymethyl-5-Fluoromethyl-Pyridine

Sulfur tetrafluoride (41 mg.-mole) is passed into 40 ml. of liquid HF, cooled in a dry-ice-acetone bath, then, acetonide of 2-methyl-3-hydroxy-4-hydroxymethyl-5-hydroxymethyl pyridine, (4.18 g.; 20 mg.-mole) is added under continuing cooling. The dry-ice-acetone bath is not replenished with dry-ice and the mixture is left standing in it overnight. After blowing off the remaining HF at room temperature, conc. aq. HCl is added, evaporated to dryness in vacuo, the residue is redissolved in 20 ml. of 1M aq. HCl, heated on the steambath for 15 minutes, (for hydrolysis of the acetonide, charcoaled and evaporated to dryness, redissolved in water, then passed through a Dowex 50 × 2 cation-exchange resin column, washed free of $F^{\ominus}$ with water.

The product, 2-methyl-3-hydroxy-4-hydroxymethyl-5-fluoromethyl pyridine, is eluted with 4M aq. HCl, the eluate is evaporated to dryness in vacuo. The dry residue is recrystallized from ethanol, to give the HCl salt, m.p. 170° C. (dec.). The novel product was characterized by C—H—N—F—Cl analysis and pmr spectrum.

EXAMPLE 12

Fluorodehydroxylation of Hexafluoro-2-Phenylisopropanol

Hydrogen fluoride (2.15 g.; 108 mg.-mole) is condensed into a KEL-F reactor (dry-ice-acetone bath); a solution of hexafluoro-phenylisopropanol, 13.1 g.; 54 mg.-mole) dissolved in 78 ml. of trichlorofluoromethane (FREON-11) is added while the reactor is cooled in dry-ice-acetone bath. $SF_4$ gas (6.1 ml. at −78° C.; 108 gm.-mole) is passed into the mixture while continuing cooling at −78° C. After aging overnight at −78° C., the solvent etc. is removed by blowing through $N_2$. Crushed ice is added, the solvent layer separated, dried over $MgSO_4$ and distilled, to give 11.25 g. of heptafluoroisopropyl benzene.

EXAMPLE 13

Fluorodehydroxylation of Choline

Choline chloride (1.32 g.; 10 ml.-mole) is dissolved in 30 ml. of liquid HF at −78° C. The solvent is evaporated and the residue redissolved in 30 ml. of liquid HF and $SF_4$ (17 mg.-mole; 1.0 ml. liquid volume) passed in with continuing cooling at −78° C. After aging overnight, an additional 13 mg.-mole amount of $SF_4$ is added and the solution left standing for four hours. The solvent is removed by evaporation at room temperature, the residue redissolved in aq. cc. HCl (approximately 10 ml.), evaporated to dryness in vacuo; this treatment is repeated four more times to result a quantitative yield of the product (2-fluoroethyl)trimethylammonium chloride. For analysis, it was recrystallized from acetonitrile-methanol. Mp.: 255°-7° C. (dec.). It was further characterized by pmr spectrum and C—H—N—F—Cl analysis.

EXAMPLE 14

Fluorodehydroxylation of Thiamine

Thiamine hydrochloride (3.5 g.; 10.3 mg.-mole) is dissolved in 30 ml. of HF at −78° C. The solvent is evaporated (to remove HCl) and the residue redissolved in 60 ml. of HF. $SF_4$ (25 mg.-mole) is passed in and the solution left aging overnight. The above operations are performed at −78° C. (dry-ice-acetone bath). The solvent is removed by evaporation at up to room temperature, the residue dissolved in water, passed through an ion-exchange resin column in the $H^{\ominus}$ form (DOWEX 50 × 2), washed with water. The product is eluted with cc. aq. HCl, the residue of which is practically pure HCl salt of fluorodeoxy thiamine chloride hydrochloride [3-(4-amino-2 methylpyrimidyl-5-methyl)-4-methyl-5-(2-fluoroethyl)-thiazolium chloride hydrochloride]. The product is characterized by pmr spectrum and

EXAMPLE 15

Fluorodehydroxylation of Pyridoxine

Pyridoxine hydrochloride (1.025 g.; 5 mg.-mole) is dissolved in 30 ml. of liquid HF, the solvent is evaporated and the residue redissolved in 30ml. of HF. AT −78° C., 2 ml. of SF$_4$ (34 mg.-moles) is passed in and the mixture left standing overnight at −78° C. The solvent is evaporated, the residue redissolved in water, passed through DOWEX 50 × 4 cation-exchange resin column. The column is washed with water, the product is eluted by conc. aqueous HCl; the residue of the eluate is in nearly quantitative yield the HCl salt of the product 2-methyl-3-hydroxy-4,5-bis-fluoromethylpyridine HCl which was recrystallized and characterized by pmr spectrum and C—H—N—F—Cl analysis.

EXAMPLE 16

Fluorodehydroxylation of β-Hydroxy-Histamine

βHydroxyhistamine dihydrochloride (0.50 g.; 2 mg.-mole) is dissolved in 15 ml. of liquid HF, the solvent blown off with nitrogen and the residue redissolved in 20 ml. of HF. SF$_4$ (liquid vol. 3 ml.) is added at −78° C. and the resulting solution kept in ice-bath overnight. The solvent is evaporated, the residue dissolved in water and passed through a DOWEX 50 × 2 cation-exchange resin column, washed with water and eluted with 2.5 M aq. HCl. The evaporated residue represents practically pure product (dihydrochloride of 4-[2-amino-1-fluoro(ethyl)]-imidaxole which was recrystallized from methanol-diethylether and characerized by C—H—N—F—Cl analysis and pmr spectrum.

EXAMPLE 17

Fluorodehydroxylation of 4-Hydroxypiperidine

4-Hydroxypiperidine (2.0 g.; 20 mg.-mole) is dissolved in 20 ml. of liq. HF at −78° C. and SF$_4$ (2 ml. liq. vol.; 55 mg.-mole) is passed in at −78° C. It is left standing overnight, gradually reaching room temperature. The solvent is removed by evaporation and the residue passed through a DOWEX 50 × 2, H$^⊕$ form. The column is washed with water and eluted with aq. 4 M HCl. The HCl eluate is evaporated to dryness in vacuo and the residue recrystallized from acetonitrile-ethylacetate mixture. The product 4-fluoropiperidine hydrochloride has a m.p. of 163°-164° C., and was characterized by pmr spectrum and C—H—N—F—Cl analysis.

EXAMPLE 18

Fluorodehydroxylation of 4-Methyl-5(2-Hydroxyethyl)Thiazole

4-Methyl-5-(2-hydroxyethyl)thiazole (2.5 g.; 17.4 mg.-mole) is dissolved in 20 ml. of liq. HF at −78° C. and SF$_4$ (2 ml. liq. vol. at −78 20 C.; 34.8 mg.-mole) is passed in. After three hours standing at −78° C, the solvent is evaporated and the aqueous solution of the residue passed through a DOWEX 50 × 2 cation-exchange column, H$^⊕$ cycle. The column is washed with water and eluted with 1 M aq. HCl. Evaporation of this eluate provides hydrochloride of the product, 4-methyl-5(2-fluoroethyl)thiazole hydrochloride. For analysis, it was purified by sublimation in vacuo and recrystallized from ethyl acetate-acetonitrile. Mp.: 106°-110° and characterized by C—H—N—F—S—Cl analysis and pmr spectrum.

EXAMPLE 19

Fluorodehydroxylation of Threo-Phenylserine

Into a solution of SF$_4$ (2.5 ml. at −78° C.; 42 mg.-mole) in 40 ml. of liq. HF, cooled in a dry-ice-acetone bath, threo-phenylserine monohydrate (1.22 g.; 10 mg.-mole) is added with stirring. After 45 minutes of aging at −78° C., the solvent is evaporated and the residue treated with 15 ml. conc. aq. HCl. Evaporation of the solvent in vacuo gives the hydrochloride of β-fluorophenylalanine is quantitative yield. The free amino acid is liberated by dissolving this salt in 3 vol.-s of water and adding 1 equiv. of pyridine. The crystalline product β-fluorophenyl-alanine is filtered, washed with isopropanol and dried. The compound is fully characterized by C—H—N—F analysis and pmr spectrum.

EXAMPLE 20

Fluorodehydroxylation of 3-Aminopropanol

3-Aminopropanol (0.8 ml.) is dissolved in 25 ml. of liq. HF at −78° C.; 2.5 ml. of SF$_4$ is passed in and the solution aged overnight at −78° C. Evaporation of solvent gives a mixture of the HF salts of the above shown products.

Separation by elution chromatography on DOWEX 50 cation-exchange resin column. Elution with water, 0.5 M aq. HCl, then with 1 M aq. HCl, then with 1 M aq. HCl. 15 ml. fractions are collected. Evaporation of fractions No. 60-69 gives 1-amino-2-fluoropropane HCl salt, whereas from fractions No. 80-89 the HCl salt of 1-amino-3-fluoropropane is obtained.

The products were fully characterized by C—H—N—F—Cl analysis and pmr spectrum.

What is claimed is:

1. The process for preparing the fluorodehydroxyl derivatives of organic alcohols selected from the group consisting of D-serine, 2-deutero-D-serine, D,L-serine, 2-deutero-D,L-serine, L-serine, and 2-deutero-L-serine using SF$_4$ in liquid hydrogen fluoride as the fluorinating agent, comprising conducting the reaction at a temperature of between about −80° C. to about +20° C. until the reaction is complete, and recovering the desired product.

2. The process of claim 1 in which the organic alcohol is D-serine.

3. The process of claim 1 in which the organic alcohol is 2-deutero-D-serine.

4. The process of claim 1 in which the organic alcohol is D,L-serine.

5. The process of claim 1 in which the organic alcohol is 2-deutero-D,L-serine.

6. The process of claim 1 in which the organic alcohol is L-serine.

7. The process of claim 1 in which the organic alcohol is 2-deutero-L-serine.

* * * * *